(12) United States Patent
Takasu et al.

(10) Patent No.: US 7,192,535 B2
(45) Date of Patent: Mar. 20, 2007

(54) CONJUGATED MOLECULE AND ELECTROLUMINESCENT DEVICE THEREOF AND ELECTRONIC DEVICE HAVING THE ELECTROLUMINESCENT DEVICE

(75) Inventors: Takako Takasu, Kanagawa (JP); Hiroko Yamazaki, Kanagawa (JP); Satoshi Seo, Kanagawa (JP); Ryoji Nomura, Kanagawa (JP); Hideko Inoue, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 413 days.

(21) Appl. No.: 10/798,410

(22) Filed: Mar. 12, 2004

(65) Prior Publication Data
US 2004/0258954 A1 Dec. 23, 2004

(30) Foreign Application Priority Data

Mar. 14, 2003 (JP) ............................. 2003-070780
Mar. 14, 2003 (JP) ............................. 2003-070806

(51) Int. Cl.
*C09K 11/54* (2006.01)
*H01J 1/62* (2006.01)
*B32B 9/00* (2006.01)
*C07D 409/00* (2006.01)

(52) U.S. Cl. ................. 252/301.16; 313/498; 428/690; 428/917; 549/59

(58) Field of Classification Search ........... 252/301.16; 313/498; 428/690, 917; 549/59
See application file for complete search history.

(56) References Cited

U.S. PATENT DOCUMENTS

| 4,720,432 | A | 1/1988 | VanSlyke et al. | |
|---|---|---|---|---|
| 6,359,150 | B1* | 3/2002 | Fukudome et al. | 549/59 |
| 6,716,995 | B2* | 4/2004 | Zhu et al. | 549/62 |
| 6,797,848 | B2* | 9/2004 | Hosokawa et al. | 585/26 |
| 6,806,374 | B2* | 10/2004 | Heeney et al. | 549/59 |
| 6,825,358 | B2* | 11/2004 | Afzali-Ardakani et al. | 549/59 |
| 6,878,801 | B2* | 4/2005 | Fujiki et al. | 528/380 |
| 6,890,715 | B1* | 5/2005 | Lewis et al. | 435/6 |
| 6,936,190 | B2* | 8/2005 | Yoshida | 252/511 |
| 6,984,737 | B2* | 1/2006 | Hartmann et al. | 549/68 |
| 7,015,336 | B2* | 3/2006 | Reed et al. | 549/59 |
| 7,029,606 | B2* | 4/2006 | Dalton et al. | 252/582 |
| 7,057,054 | B2* | 6/2006 | Irie | 549/59 |

OTHER PUBLICATIONS

Pepitone, M. et al. "Synthesis and Characterization of Photoluminescent 3,4-Ethylenedioxythiophene Derivatives", Chem. Mater. 2003, vol. 15, pp. 557-563.
Groenendaal. L. et al. "Poly(3,4-Ethylenedioxythiophene) And Its Derivatives: Past, Present, And Future" Advanced Materials, 2000, vol. 12, No. 7, pp. 481-494.
International Search Report (Application No. PCT/JP2004/003101) Dated Jul. 20, 2004 (In Japanese).
Written Opinion (Application No. PCT/JP2004/003101) Dated Jul. 20, 2004 (Partial Translation).
Shirota Y. et al. "Multilayered Organic Electroluminescent Device Using a Novel Starburst Molecule, 4,4', 4"-tris(3-methylphenylamino)triphenylamine, as a hole transport material" Appl. Phys. Lett. 65(7) Aug. 15, 1994, pp. 807-809.
Van Slyke, S.A., et al. "Organic Electroluminescent Devices With Improved Stability", Appl. Phys. Lett. 69 (15) Oct. 7, 1996, pp. 2160-2162.
Yang Y. et al.. "Polyaniline as a Transparent Electrode for Polymer Light-Emitting Diodes: Lower Operating Voltage and Higher Efficiency" Appl. Lett. 64 (10), Mar. 7, 1994, pp. 1245-1247.
Carter, S.A. et al. "Polymeric Anodes for Improved Polymer Light-Emitting Diode Performance" Appl. Phys. Lett. 70 (16) Apr. 21, 1997, pp. 2067-2069.
S. Tokito et al., "Metal Oxides as a Hole-Injecting Layer for an Organic Electroluminescent Device", J. Appl. Phys. (Journal of Applied Physics), 1996, vol. 29, pp. 2750-2753.

* cited by examiner

*Primary Examiner*—Deborah C. Lambkin
(74) *Attorney, Agent, or Firm*—Nixon Peabody LLP; Jeffrey L. Costellia

(57) ABSTRACT

It is intended to provide a novel material having no absorption or low absorption intensity in the visible region and to provide an electroluminescent device excellent in hole injection characteristic by using the novel material. A novel organic material wherein two electron abundant aromatic rings inherently having a low ionization potential, such as a thiophene ring, a furan ring, and pyrrol ring, is intervened by a conjugated substituent such as a phenylene ring is provided. The electroluminescent device having an excellent hole injection characteristic is provided by using this novel organic material.

20 Claims, 11 Drawing Sheets

CONJUGATED MOLECULE AND ELECTROLUMINESCENT DEVICE THEREOF AND ELECTRONIC DEVICE HAVING THE ELECTROLUMINESCENT DEVICE

FIELD OF THE INVENTION

The present invention belongs to a technical field relating to a display device wherein a device (hereinafter referred to as electroluminescent device) having a structure that a thin film which emits light owing to a phenomenon called electroluminescence (hereinafter abbreviated to EL) is sandwiched between an anode and a cathode is provided on a substrate.

BACKGROUND ART

A display for displaying images is one of light emitting devices indispensable in the modern life and takes various forms such as a so-called TV monitor, a liquid crystal display developed rapidly in recent years, an organic EL display expected to be developed, and the like depending on the usage. Among the above, the organic EL display is best noted as a next generation flat panel display device.

A light emission mechanism of an electroluminescent device constituting the organic EL display is such that a luminescent layer made from a luminescent composition is provided between electrodes so that electrons injected from a cathode are recombined with holes injected from an anode at the recombination center of the luminescent layer to form molecular excitons when a current is supplied and photons discharged when the molecular excitons return to the ground state are used for the light emission. Accordingly, one of preconditions for manufacturing a light emitting device of good efficiency is to inject the holes and the electrons efficiently into the luminescent layer made of an organic thin film or the like.

Under typical electroluminescent device operation conditions, a current of about 100 mA/cm$^2$ is injected into the organic thin film inherently having a high electrical resistance. In order to realize such high density current injection, it is necessary to keep the sizes of a barrier against the holes injected from the anode and a barrier against the electrons injected from the cathode as small as possible. That is to say, it is necessary to use a metal having a small work function for the cathode and to select an electrode having a large work function for the anode. By selecting various metals and alloys for the cathode, it is practically possible to control the work function at will. In contrast, since transparency is required of the anode in general electroluminescent devices, the material to be used for the anode is limited to transparent conductive oxides under the current situation, and there is no alternative but to select some oxide conductive films such as an indium-tin oxide (hereinafter abbreviated to ITO) film in view of stability, transparency, resistivity, and the like at present. A work function of the ITO film can be changed to a certain degree by a history of film formation and a surface treatment, but such process has its limit. This inhibits the reduction in the hole injection barrier.

As one of methods to reduce the barrier against hole injection from the ITO cathode, an insertion of a buffer layer on the ITO film is known. By optimizing an ionization potential of the buffer layer, it is possible to reduce the hole injection barrier. The above-described buffer layer is called a hole injection layer. Materials which can function as the hole injection layer are generally classified into metal oxides, low molecular organic compounds, and high molecular compounds. Examples of the metal oxides are vanadium oxide, molybdenum oxide, ruthenium oxide, aluminum oxide, and the like (Non-Patent Documents 1 and 2). Examples of the low molecular organic compounds are starburst amines (Non-Patent Document 3) such as m-MTDATA, metal phthalocyanine (Patent Document 1, Non-Patent Document 4), and the like. As the high molecular compounds materials, conjugated polymers such as polyaniline (Non-Patent Document 5) and a polythiophene derivative (Non-Patent Document 6) are known. By using the above-described materials for the hole injection layer, the hole injection barrier is reduced and the holes are efficiently injected, thereby improving the efficiency and life of the electroluminescent device and reducing a driving voltage.

[Non-Patent Document 1]
S. Tokito, Et al., J. Phys. D 1996, 29, 2750–2753

[Non-Patent Document 2]
Tsunataka Kurosaka, et al., Shingakugiho, 1998, 98, 63–68

[Non-Patent Document 3]
Y Shirota, et al., Appl. Phys. Lett. 1994, 65, 807–809

[Patent Document 1]
S. A. Vanslyke, et al., U.S. Pat. No. 4,720,432

[Non-Patent Document 4]
S. A. Vanslyke, et al., Appl. Phys. Lett. 1996, 69, 2160–2162

[Non-Patent Document 5]
Y. Yang, et al., Appl. Phys. Lett. 1994, 64, 1245–1247

[Non-Patent Document 6]
S. A. Carter, et al., Appl. Phys. Lett. 1997, 70, 2067–2069

Among the above-described materials, the low molecular compounds such as the starburst amines and the metal phthalocyanine, and the high molecular materials such as polyaniline are frequently used (see, for example, Patent Documents 5 and 6). Particularly, copper phthalocyanine is one of the most-frequently-used hole injection materials. This material can be obtained easily and is chemically and thermally stable. However, metal phthalocyanines have a remarkably low solubility and it is difficult to chemically modify the compounds. Further, though the materials have excellent characteristics as the hole injection material, they are colored in many cases to disadvantageously color a light emission surface itself of the device. Therefore, there is a demand for an electroluminescent device using a hole injection material having no absorption or small absorption intensity in the visible region.

DISCLOSURE OF THE INVENTION (Problems to be Solved by the Invention)

The present invention has been accomplished in view of the above problems, and an object thereof is to provide a novel material having no absorption or small absorption intensity in the visible region and to provide an electroluminescent device excellent in hole injection characteristic by using the novel material for an electroluminescent device.

(Means for Solving the Problems)

This invention has configurations of the following (1) to (7).

(1) An electroluminescent device comprising a conjugated molecule represented by the general formula [Chem. 5]

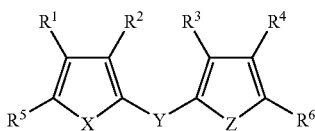

[Chem. 5]

(wherein X and Z may be the same or different and represent a sulfur atom, an oxygen atom, or a nitrogen atom and a silicon atom each having an alkyl group or an arylen group; Y represents an arylen group; and $R^1$ to $R^6$ independently represent a hydrogen atom, an aryl group, an alkyl group, a cyano group, a dialkylamino group, a thioalkoxy group, or an alkoxy group).

(2) An electroluminescent device comprising a conjugated molecule represented by the general formula [chem. 6]

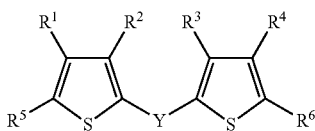

[Chem. 6]

(wherein Y represents an arylen group; and $R^1$ to $R^6$ independently represent a hydrogen atom, an aryl group, an alkyl group, a cyano group, a dialkylamino group, a thioalkoxy group, or an alkoxy group).

(3) An electroluminescent device comprising a conjugated molecule represented by the general formula [chem. 7]

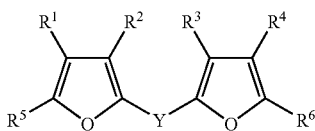

[Chem. 7]

(wherein Y represents an arylen group; and $R^1$ to $R^6$ independently represent a hydrogen atom, an aryl group, an alkyl group, a cyano group, a dialkylamino group, a thioalkoxy group, or an alkoxy group).

(4) An electroluminescent device comprising a conjugated molecule represented by the general formula [chem. 8]

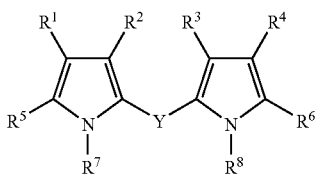

[Chem. 8]

(wherein Y represents an arylen group; $R^1$ to $R^6$ independently represent a hydrogen atom, an aryl group, an alkyl group, a cyano group, a dialkylamino group, a thioalkoxy group, or an alkoxy group; and $R^7$ and $R^8$ represent an alkyl group or an aryl group).

(5) The conjugated molecule represented by the general formula [chem. 5] (wherein X and Z may be the same or different and represent an oxygen atom, a sulfur atom, or a silicon atom and a nitrogen atom each having an alkyl group or an arylen group; Y represents an arylen group and represents a bivalent group having a hydrocarbon aromatic ring having 6 to 20 carbon atoms or a bivalent heteroaromatic group having 4 to 30 carbon atoms and including at least one selected from the group consisting of oxygen, nitrogen, sulfur, and silicon; $R^1$ to $R^4$ independently represent a hydrogen atom, an aryl group, an alkyl group, a cyano group, a dialkylamino group, a thioalkoxy group, or an alkoxy group; and $R^5$ and $R^6$ represents an aromatic hydrocarbon cyclic group or a heteroaromatic group including at least one selected from the group consisting of oxygen, nitrogen, sulfur, and silicon, an alkyl group, a cyano group, a dialkylamino group, a thioalkoxy group, or a silyl group).

(6) The conjugated molecule represented by the general formula [Chem. 5], which is characterized in that a solubility to chloroform at 25° C. and 1 atm. is in the range of 1 wt. % to 20 wt. %.

(7) An electric device characterized by using the electroluminescent device containing the conjugated molecule represented by the general formula [Chem. 5].

Each of the compounds represented by the general formulas [Chem. 5] to [Chem. 8] is obtainable by introducing two of electron abundant aromatic rings inherently having a low ionization potential, such as thiophene, furan, and pyrrol groups, into a conjugated molecule such as a phenylene ring. The molecule thus-designed is expected to have a low ionization potential. Particularly, when $R^1$ to $R^6$ are electron donor substituents such as the alkoxy group, it is possible to provide a molecule having a much smaller ionization potential. Therefore, the compounds are expected to indicate an excellent hole injection characteristic or hole transporting characteristic. Further, when a substituent other than a hydrogen atom is introduced into $R^5$ and $R^6$, it is possible to prevent the compound represented by the general formula [Chem. 5] from being easily polymerized by oxidation and, further, to impart solubility to the compound. Based on the above molecular designing, this invention proposes the use of the compounds represented by the general formulas [Chem. 5] to [Chem. 8] for the electroluminescent device.

The inventors of this invention have synthesized and studied in detail the novel compounds to find that each of the compounds has small absorption intensity in the visible region and is low in ionization potential. Further, they have found that it is possible to obtain compounds having a high solubility, very low absorption intensity in the visible region, and a small ionization potential by introducing a substituent other than a hydrogen atom into $R^5$ and $R^6$. Furthermore, as a result of using the compounds for electroluminescent devices, they have found that it is possible to manufacture an electroluminescent device having an excellent hole injection characteristic as described in Examples.

(Effect of the Invention)

The novel organic materials proposed by this invention are characterized by a small absorption in the visible region and a small redox potential. That is to say, the materials are excellent in hole injection characteristic. Further, compounds in each of which a substituent other than hydrogen is introduced into $R^5$ and $R^6$ have a high solubility and small crystallinity thanks to the high solubility. Therefore, it is possible to form a deposition film having a good film quality. By using the materials to an electroluminescent device, it is possible to manufacture an electroluminescent device excellent in hole injection characteristic. Further, due to the low crystallinity, a manufacture of a device having a high reliability, i.e. a long life, is expected.

BEST MODE FOR CARRYING OUT THE INVENTION

Figure 1:
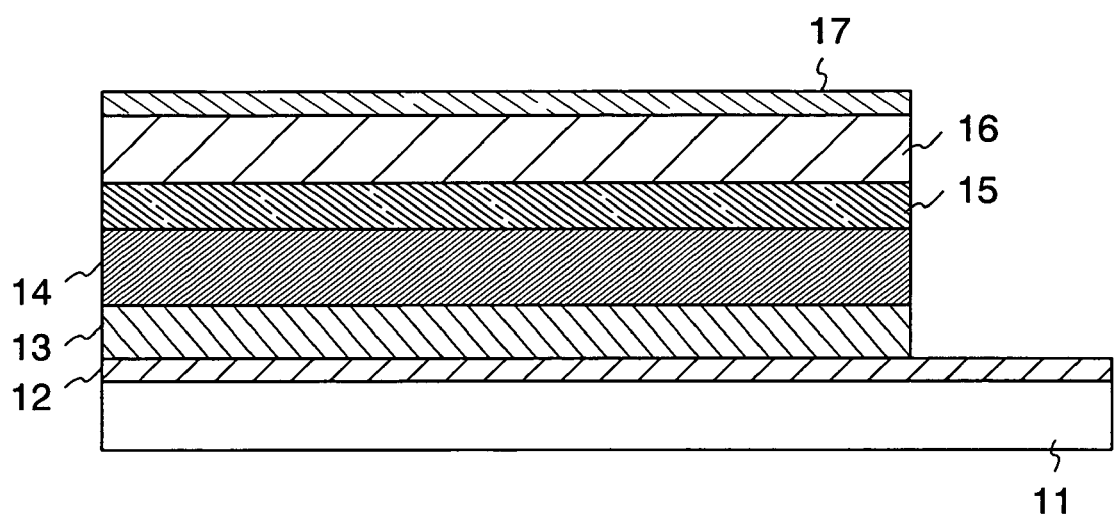
FIG. 1 is a block diagram showing an electroluminescent device to be manufactured by carrying out the present invention.

Embodiments of the present invention will hereinafter be described.

(Embodiment Mode 1)

In this embodiment mode, a structure of a compound suitable for carrying out this invention will be described. In the compound represented by the general formula [Chem. 5], X and Z may be the same or different and represent a sulfur atom, an oxygen atom, or a nitrogen atom or a silicon atom each having an alkyl group or an arylen group. The alkyl group on the nitrogen atom or the silicon atom is an aliphatic hydrocarbon group having 1 to 4 carbon atoms (a methyl group, an ethyl group, a propyl group, an isopropyl group, a sec-butyl group, a tert-butyl group, etc.) or an aliphatic cyclic hydrocarbon group having 4 to 6 carbon atoms (a cyclobutyl group, a cyclopentyl group, a cyclohexyl group, etc.). The aryl group on the nitrogen atom or the silicon atom is an aromatic group such as a phenyl group, a naphthyl group, an anthranyl group, and a prenyl group, in each of the aromatic groups a hydrogen atom may be substituted by a hydrocarbon group or an alkoxy group.

In the compounds represented by the general formulas [Chem. 5] to [Chem. 8], Y represents an aromatic substituent. More specifically, Y represents an aromatic group such as a phenylene group, a naphthylen group, an anthranylene group, and a pyrenylene group, in each of the aromatic groups a hydrogen atom may be substituted by a hydrocarbon group, an alkoxy group, a dialkylamino group, a diphenylamino group, or the like. Alternatively, Y may be a heteroaromatic group. Specific examples of the heteroaromatic group may be a pyridyl group, an indoryl group, a carbazoryl group, a thienyl group, a furyl group, and the like.

In the compounds represented by the general formulas [Chem. 5] to [Chem. 8], $R^1$, $R^2$, $R^3$, and $R^4$ represent a hydrogen atom, an alkyl group, an aryl group, a cyano group, a dialkylamino group, a diarylamino group, an alkoxy group, a thioalkoxy group, or a halogen atom. The alkyl group is an aliphatic hydrocarbon group having 1 to 6 carbon atoms (a methyl group, an ethyl group, a propyl group, an isopropyl group, a sec-butyl group, a tert-butyl group, an n-hexyl group, etc.) or an aliphatic cyclic hydrocarbon group having 4 to 6 carbon atoms (a cyclobutyl group, a cyclopentyl group, a cyclohexyl group, etc.). The aryl group is an aromatic group such as a phenyl group, a naphthyl group, an anthranyl group, and a prenyl group, in each of which a hydrogen atom may be substituted by a hydrocarbon group or an alkoxy group. Alternatively, the aryl group may be a heteroaromatic group. Specific examples of the heteroaromatic group are a pyridyl group, an indoryl group, a carbazoryl group, thienyl group, a furyl group, and the like. The dialkylamino group is a dimethylamino group, a diethylamino group, a diisopropylamine group, or the like. The diarylamino group is a substituent such as a diphenylamino group and a dinaphthylamino group, in each of which an aromatic ring may be substituted by an alkyl group or an alkoxy group. The substituents represented by $R^1$, $R^2$, $R^3$, and $R^4$ may preferably be electron donor substituents, so that it is possible to further reduce an ionization potential of a molecule by introducing an alkoxy group such as a methoxy group, an ethoxy group, and a hexyloxy group, an amino group such as a dimethylamino group, a diethylamino group, and a diphenylamino group, a thioalkoxy group having 6 or less carbon atoms, or the like. The compound may be condensated with an aryl group such as a benzene ring at substitution positions of $R^1$ and $R^2$ or positions of $R^3$ and $R^4$. More preferably, $R^1$ and $R^2$ or $R^3$ and $R^4$ may bond with a relevant thiophene ring, furan ring or pyrrol ring via a hetero atom such as a hydrogen atom to form a cyclic structure. This is because a band gap of molecules is reduced by the formation of cyclic structure, thereby reducing an oxidation potential, i.e. the ionization potential, of the compound. Thus, the hole injection characteristic is improved.

In the compounds represented by the general formulas [Chem. 5] to [Chem. 8], $R^5$ and $R^6$ represent a hydrogen atom, an alkyl group having a C1 to C6 straight chain or a branched chain, an aromatic substituent such as a phenyl group, an antholyl group, a naphthyl group, a pyridyl group, and a thienyl group, a cyano group, a dialkylamino group, a diarylamino group, an alkoxy group, a thioalkoxy group, or a halogen atom. The substituents may be bonded with a relevant aromatic ring via a carbonyl group or a carboxyl group. Alternatively, the alkyl group and the aromatic substituents may be bonded with a relevant thiophene ring, furan ring or pyrrol ring via a silicon atom. By introducing an electron donor substituent other than hydrogen preferably, such as an alkoxy group, an amino group, or a thioalkoxy group, as $R^5$ and $R^6$, it is possible to further reduce the ionization potential of molecules. Further, it is possible to suppress oxidative polymerization of the relevant heteroaromatic ring by introducing a substituent other than a hydrogen atom.

In the compound represented by the general formula [Chem. 8], $R^7$ and $R^8$ represent a hydrogen atom, an alkyl group, or an aryl group. The alkyl group is an aliphatic hydrocarbon group (a methyl group, an ethyl group, a propyl group, an isopropyl group, a sec-butyl group, a tert-butyl group, etc.) having 1 to 4 carbon atoms or an alicyclic hydrocarbon group (a cyclobutyl group, a cyclopentyl group, a cyclohexyl group, etc.) having 4 to 6 carbon atoms. The aryl group is an aromatic group such as a phenyl group, a naphthyl group, an anthranyl group, and a pyrenyl group, in each of which a hydrogen atom may be substituted by a hydrocarbon group, an alkoxy group, or the like.

(Embodiment Mode 2)

In this embodiment mode, a basic structure of an electroluminescent device using the compounds represented by the general formulas [Chem. 5] to [Chem. 8] will be described with reference to FIG. 1. A device structure described in this embodiment mode of the invention is such that, but not limited to, a hole injection layer, a hole transporting layer, a luminescent layer, and an electron transporting layer are provided between a cathode and an anode, and various electroluminescent device structures such as an anode/hole injection layer/luminescent layer/electron transporting layer/cathode, an anode/hole injection layer/hole transporting layer/luminescent layer/electron transporting layer/electron injection layer/cathode, an anode/hole injection layer/hole transporting layer/luminescent layer/hole blocking layer/electron transporting layer/cathode, an anode/hole injection layer/hole transporting layer/luminescent layer/hole blocking layer/electron transporting layer/electron injection layer/cathode, and so forth may be employed. In these electroluminescent devices, the above-described compounds may be used for the hole injection layer, the hole transporting layer, or the luminescent layer.

Referring to FIG. 1, a substrate made from a glass, a quartz, a transparent plastic may be used as a substrate 11 supporting the electroluminescent device. It is preferable to use a metal, an alloy, an electroconductive compound, a mixture thereof, and the like having a large work function (4.0 eV or more) as a cathode 12. Specific examples of the anode materials are ITO, IZO (indium zinc oxide) obtainable by adding 2 to 20% zinc oxide (ZnO) to indium oxide, gold (Au), platinum (Pt), nickel (Ni), tungsten (W), chrome (Cr), molybdenum (Mo), iron (Fe), cobalt (Co), copper (Cu), palladium (Pd), a nitride of a metallic material (TiN), and the like.

The materials proposed by this invention, i.e. the compounds represented by the general formulas [Chem. 5] to [Chem. 8], are used for a hole injection layer 13. A known material may be used for a hole transporting layer 14. Typical examples of the known material are aromatic amine based compounds such as 4,4'-bis[N-(1-naphthyl)-N-phenyl-amino]-biphenyl (hereinafter referred to as α-NPD), 4,4',4''-tris(N,N-diphenyl-amino)-triphenylamine (hereinafter referred to as TDATA), 4,4',4''-tris[N-(3-methylphenyl)-N-phenyl-amino]-triphenylamine (hereinafter referred to as MTDATA) and like starburst aromatic amine compounds. Denoted by 15 is a luminescent layer which may be a known one, and a metal complex such as tris(8-quinolinolato) aluminum (hereinafter referred to as $Alq_3$), tris(4-methyl-8-quinolinolato)aluminum (hereinafter referred to as $Almq_3$), bis(10-hydroxybenzo[η]-quinolinato)beryllium (hereinafter referred to as $BeBq_2$), bis(2-methyl-8-quinolinolato)-(4-hydroxy-biphenylyl)-aluminum (hereinafter referred to as BAlq), bis[2-(2-hydroxyphenyl)-benzooxazolato]zinc (hereinafter referred to as $Zn(BOX)_2$), and bis[2-(2-hydroxyphenyl)-benzothiazolato]zinc (hereinafter referred to as $Zn(BTZ)_2$) and various fluorescent dyes are effectively used for the luminescent layer 15. In addition, as described in Embodiments, the compounds proposed by this invention, i.e. the materials represented by the general formulas [Chem. 5] to [Chem. 8], are usable for the luminescent layer 15 since they have the light emitting capability. Known materials are usable for an electron transporting layer 16. More specifically, it is preferable to use a metal complex having a quinoline skeleton or a benzoquinoline structure, such as a tris(8-quinolinolato)aluminum complex (hereinafter referred to as $Alq_3$) as well as a mixed ligand complex of the metal complex. Further, it is possible to use, in addition to the metal complex, an oxadiazole derivative such as 2-(4-biphenylyl)-5-(4-tert-butylphenyl)-1,3,4-oxadiazole (hereinafter referred to as PBD) and 1,3-bis[5-(p-tert-butylphenyl)-1,3,4-oxadiazole-2-yl]benzene (hereinafter referred to as OXD-7); a triazole derivative such as 3-(4-tert-butylphenyl)-4-phenyl-5-(4-biphenyl)-1,2,4-triazole (hereinafter referred to as TAZ) and 3-(4-tert-butylphenyl)-4-(4-ethylphenyl)-5-(4-biphenylyl)-1,2,4-triazole (hereinafter referred to as p-EtTAZ); and a phenanthroline derivative such as basophenanthroline (hereinafter referred to as BPhen) and basocuproine (hereinafter referred to as BCP).

In the device shown in FIG. 1, a cathode 17 is formed on each of the functional layers. It is preferable to use a metal, an alloy, a conductive compound, a mixture thereof, and the like having a small work function for the cathode. More specifically, it is possible to form the cathode by using a transition metal containing a rare earth metal in addition to a typical device of the first or second group, i.e., an alkali metal such as Li and Cs, an alkaline earth metal such as Mg, Ca, and Sr, an alloy (Mg:Ag, Al:Li) containing the alkali metal and the alkaline earth metal, and a compound containing the alkali metal and the alkaline earth metal (LiF, CsF, $CaF_2$), and, also, it is possible to form the cathode by laminating metals (including alloys) such as Al, Ag, and ITO.

The above described anode materials and cathode materials are formed by vapor deposition, sputtering, and so forth. A thickness of each of the materials may preferably be from 10 to 500 nm.

Electrons injected from the cathode are recombined with the holes injected from the anode upon conduction between the electrodes of the electroluminescent device shown in FIG. 1, thereby producing light emission.

(Embodiment Mode 3)

Figure 2:
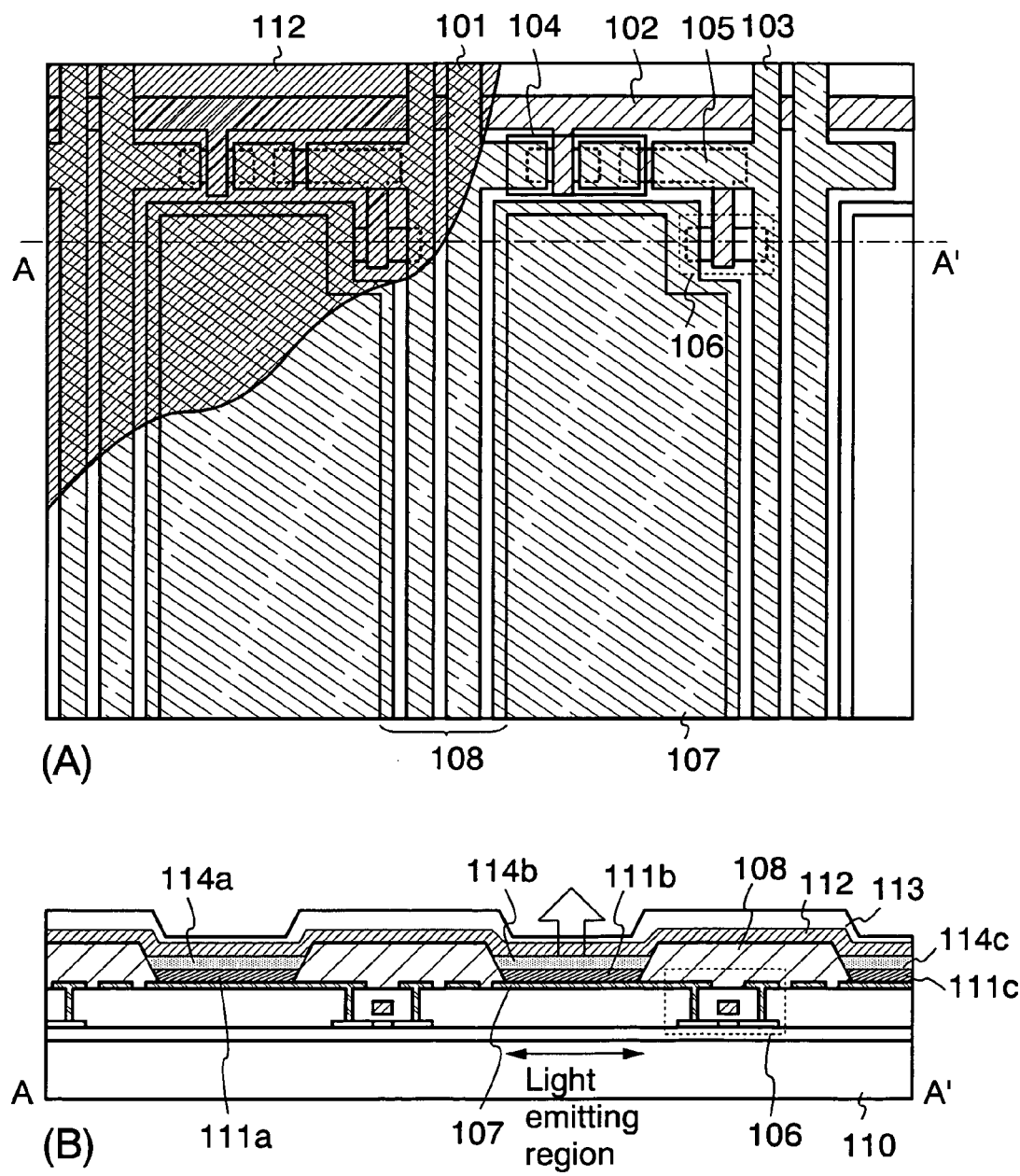
FIG. 2 is a diagram showing a light emitting apparatus to be manufactured by carrying out this invention.

In this embodiment mode, an electroluminescence device to be manufactured on a substrate on which a TFT has been mounted will be described using FIG. 2.

In a pixel structure shown in FIG. 2(A), denoted by 101 is a data signal line; denoted by 102 is a gate signal line; denoted by 103 a power line; denoted by 104 is a TFT for switching (hereinafter referred to as a switching TFT); denoted by 105 is a condenser for charge retention; denoted by 106 is a TFT for driving (hereinafter referred to as a driving TFT) which serves to supply a current to the electroluminescent device; and denoted by 107 is a pixel electrode connected to a drain of the driving TFT, which functions as an anode of the light emitting device. Denoted by 112 is an opposed electrode which functions as a cathode of the light emitting device.

Shown in FIG. 2(B) is a diagram corresponding to a section indicated by the line A–A'. In FIG. 2(B), denoted by 110 is a substrate, and it is possible to use a glass substrate, a quartz substrate, a plastic substrate, or other transparent substrate as the substrate. The driving TFT 106 is formed over the substrate 110 by semiconductor processing. Further, an insulator 108 which is patterned to have a lattice-like form is provided in such a fashion as to cover edges of pixel electrodes 107 so formed as to be connected to the driving TFT 106 and at least the driving TFT and the switching TFT.

Hole injection layers 111a to 111c are formed on the pixel electrodes 107 using the compounds represented by the general formulas [Chem. 5] to [Chem. 8], and then functional layers 114a to 114c including a luminescent layer are laminated. After that, the opposed electrode 112 functioning as the anode and a passivation film 113 are formed. The functional layers 114a to 114c means a hole transporting layer, a luminescent layer, an electron transporting layer, an electron injection layer, a hole blocking layer, an electron blocking layer, an organic compound or an inorganic compound contributing to the recombination of carriers, or a stacked body thereof. It is possible to use the compounds described in Embodiment 2 for the layers.

An aluminum film containing a device belonging to the first or second group of the periodic table, a silver thin film, or the like may be used as the opposed electrode 112, and, in this embodiment, a film thickness thereof may desirably be 50 nm or less because the film is required to allow the light emitted from the functional layers 114a to 114c including the luminescent layer to pass therethrough. Further, usable as the passivation film 113 are a silicon nitride film, an aluminum nitride film, a diamond-like carbon film, or an insulating film having a high blocking property to moisture and oxygen.

(Embodiment Mode 4)

Figure 3:
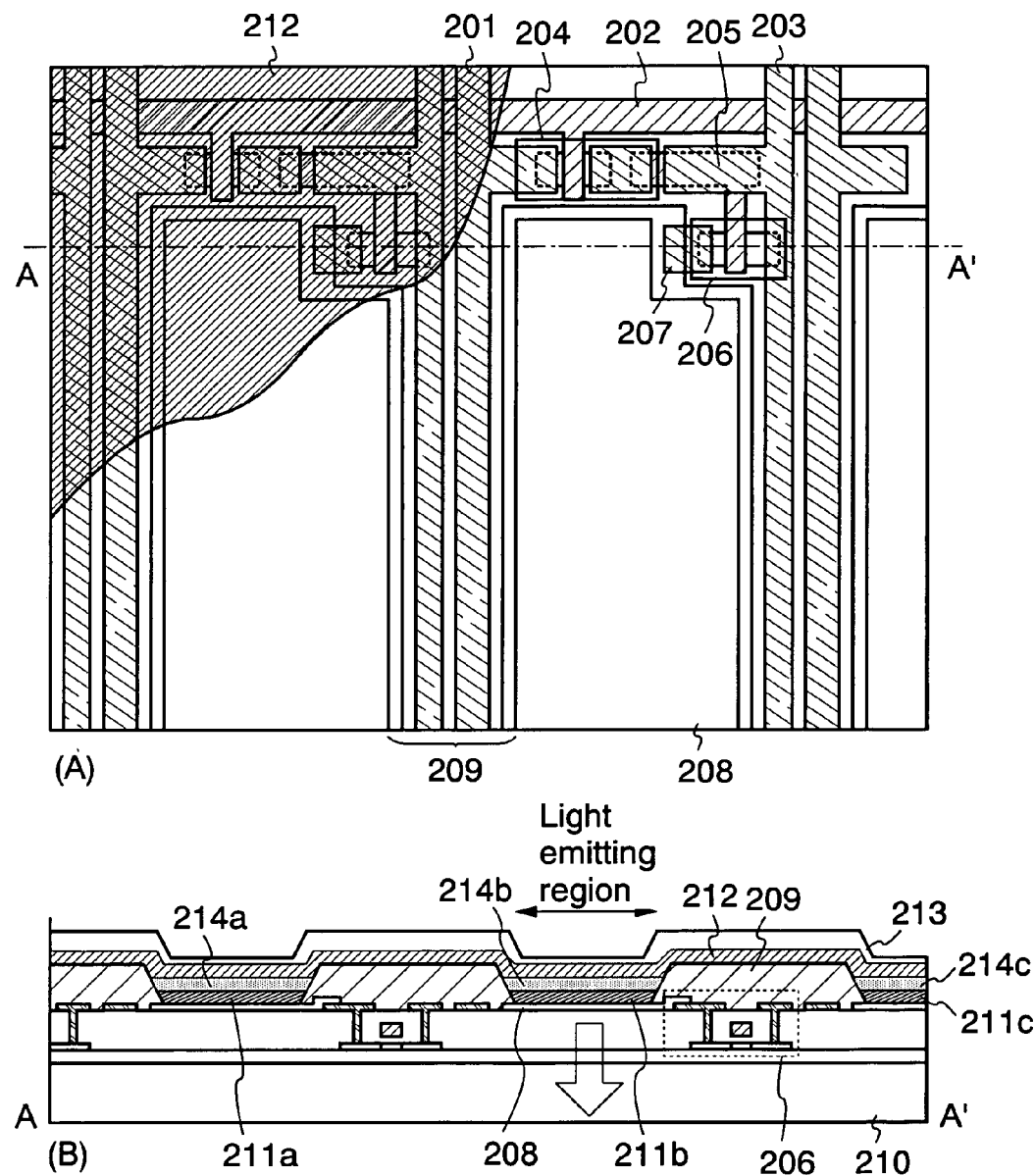
FIG. 3 is a diagram showing a light emitting apparatus to be manufactured by carrying out this invention.

In this embodiment mode, an example of the electroluminescent device to be manufactured on the substrate on which the TFT has been mounted will be described using FIG. 3.

In the pixel structure shown in FIG. 3(A), denoted by 201 is a data signal line; denoted by 202 is a gate signal line; denoted by 203 is a power line; denoted by 204 is a switching TFT; denoted by 205 is a condenser for charge retention; denoted by 206 is a driving TFT; denoted by 207 is a drain electrode of the driving TFT; and denoted by 208 is a pixel electrode connected to the drain electrode of the driving TFT, which functions as an anode of a light emitting device. It is preferable to use a conductive film which is transparent to visible rays as the pixel electrode 208 in order that the light emitted from the luminescent layer passes therethrough, and an oxide conductive film made from ITO (a compound of indium oxide and tin oxide) or a compound of indium oxide and zinc oxide may preferably be used as the pixel electrode 208. Further, denoted by 212 is an opposed electrode which functions as a cathode of the light emitting device.

Shown in FIG. 3(B) is a diagram corresponding to a section indicated by the line A–A'. In FIG. 3(B), denoted by 210 is a substrate, and it is possible to use a glass substrate, a quartz substrate, a plastic substrate, or any other transparent substrate as the substrate. The driving TFT 206 is formed over the substrate 210 by semiconductor processing. Further, an insulator 209 which is patterned to have a lattice-like form is provided in such a fashion as to cover edges of the pixel electrodes 208 so formed as to be connected to the driving TFT 206 and at least the driving TFT and the switching TFT.

Hole injection layers 211a to 211c are formed on the pixel electrodes 208 using the compounds represented by the general formulas [Chem. 5] to [Chem. 8]. Then functional layers 214a to 214c including a luminescent layer are laminated. The functional layers 214a to 214c means a carrier injection layer, a carrier transporting layer, a carrier blocking layer, the luminescent layer, an organic compound or an inorganic compound contributing to the recombination of carriers, or a stacked body thereof. Known materials may be used for the laminated structure and as the materials of the functional layers 214a to 214c.

An aluminum film containing a device belonging to the first or second group of the periodic table, a silver thin film, or the like may be used as the opposed electrode 212. Further, usable as a passivation film 213 are a silicon nitride film, an aluminum nitride film, a diamond-like carbon film, or an insulating film having a high blocking property to moisture and oxygen.

(Embodiment Mode 5)

In this embodiment mode, a basic structure of a device to be used for achieving white light emission by doping with a fluorescent material (hereinafter referred to also as a dopant) in an electroluminescent device formed by using the materials proposed by this invention, i.e. the materials represented by the general formulas [Chem. 5] to [Chem. 8]. In addition, it is also possible to apply this device structure to the substrate on which the TFT has been mounted as described in Embodiments 2 and 3.

In FIG. 4(A), denoted by 301 is a substrate, and a glass substrate, a quartz substrate, or a plastic substrate may be used as the substrate. A anode 302 which is a transparent conductive film made from ITO is formed on 301. After that, the blue luminescent compounds represented by the general formulas [Chem. 5] to [Chem. 8] are formed into films by vapor deposition, and, in the film formation, a dopant (green) 312 which emits green light by absorbing fluorescence discharged from the blue luminescent compound 311 and a dopant (red) 313 which emits red light by absorbing fluorescence discharged from the blue luminescent compound 311 are deposited at the same time. It is possible to use existing materials as the dopants, and specific examples thereof are quinacridone, dialkylquinacridone, rubrene, perylene, DPT, DCM, organic metal compounds capable of triplet emission, such as tris(2-phenylpirydine)iridium and 2,3,7,8,12,13,17,18-octaethyl-21H,23H-porphyrin-platinum complex, and the like. Thus, the luminescent layer which is doped with the dopants (312, 313) is formed on ITO.

After that, a cathode 320 is formed by sputtering or vapor deposition. The structure shown in FIG. 4(A) is one of the most basic structures of the white electroluminescent device. Accordingly, it is possible to introduce a hole injection layer, a hole transporting layer, an electron transporting layer, or an electron injection layer in addition to the luminescent layer.

Figure 4:
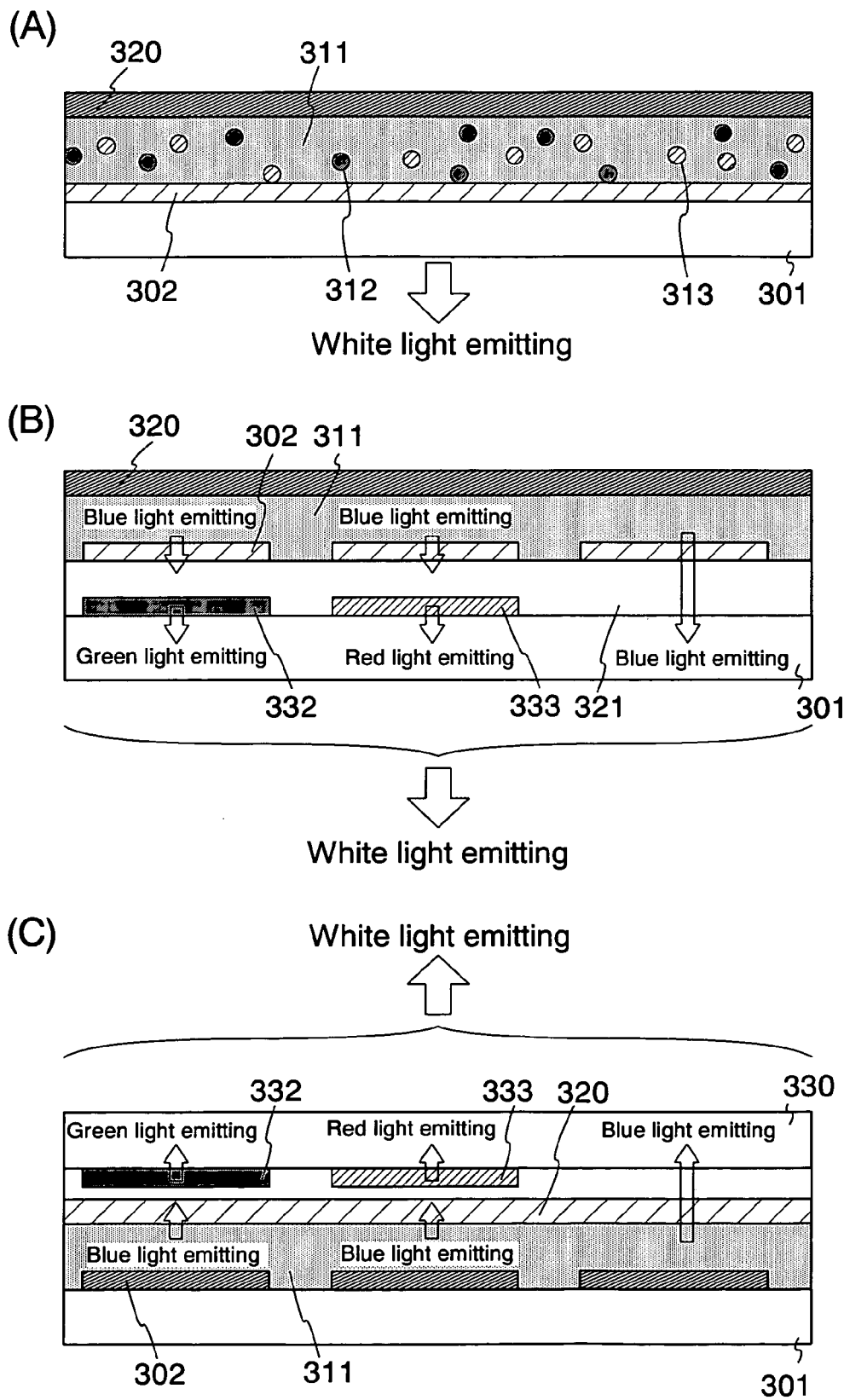
FIG. 4 is a diagram showing a basic structure of a white light emitting apparatus obtainable by carrying out this invention.

In the light emitting device shown in FIG. 4, not only the blue light emitted from the blue luminescent compound 311, but also the green light and the red light emitted from the dopants (312, 313) which absorb the blue light for the light emission are observed. It is possible to obtain the white light by causing the light of the three primary colors to be emitted simultaneously.

Alternatively, it is possible to obtain the white light by device structures shown in FIGS. 4(B) and 4(C).

The structure shown in FIG. 4(B) is obtainable by: patterning a color conversion layer (green) 332 made from a fluorescent material which emits green light by absorbing fluorescent discharged from the blue luminescent compound 311 and a color conversion layer (red) 333 made from a fluorescent material which emits red light by absorbing fluorescent discharged from the blue luminescent compound 311 on the substrate; forming an insulating film 321 on the color conversion layers; forming the blue luminescent compound 311 after patterning the anode 302; and forming the cathode 320 thereon. In this case, the anode 302 has transparency, and the cathode 320 has light shielding property; therefore, the white light is obtained from the substrate 301 side.

The structure shown in FIG. 4(C) is obtainable by patterning the anode 302 on the substrate; forming the blue luminescent compound 311, and forming the cathode 320 thereon. In turn, a color conversion layer (green) 332 made from a fluorescent material which emits green light by absorbing fluorescent discharged from the blue luminescent compound 311 and a color conversion layer (red) 333 made from a fluorescent material which emits red light by absorbing the fluorescent discharged from the blue luminescent compound 311 are patterned on an opposed substrate 330, and the structure is obtained by joining the opposed substrate 330 to the substrate 301. In this case, the anode 302 has light shielding property, and the cathode 320 has transparency; therefore, the white light is obtained from the opposed substrate 330 side.

The electroluminescent device emitting the white light as described in this embodiment may be used as illuminating apparatus and the like, and the illuminating apparatus are encompassed by this invention.

(Embodiment Mode 6)

Figure 5:
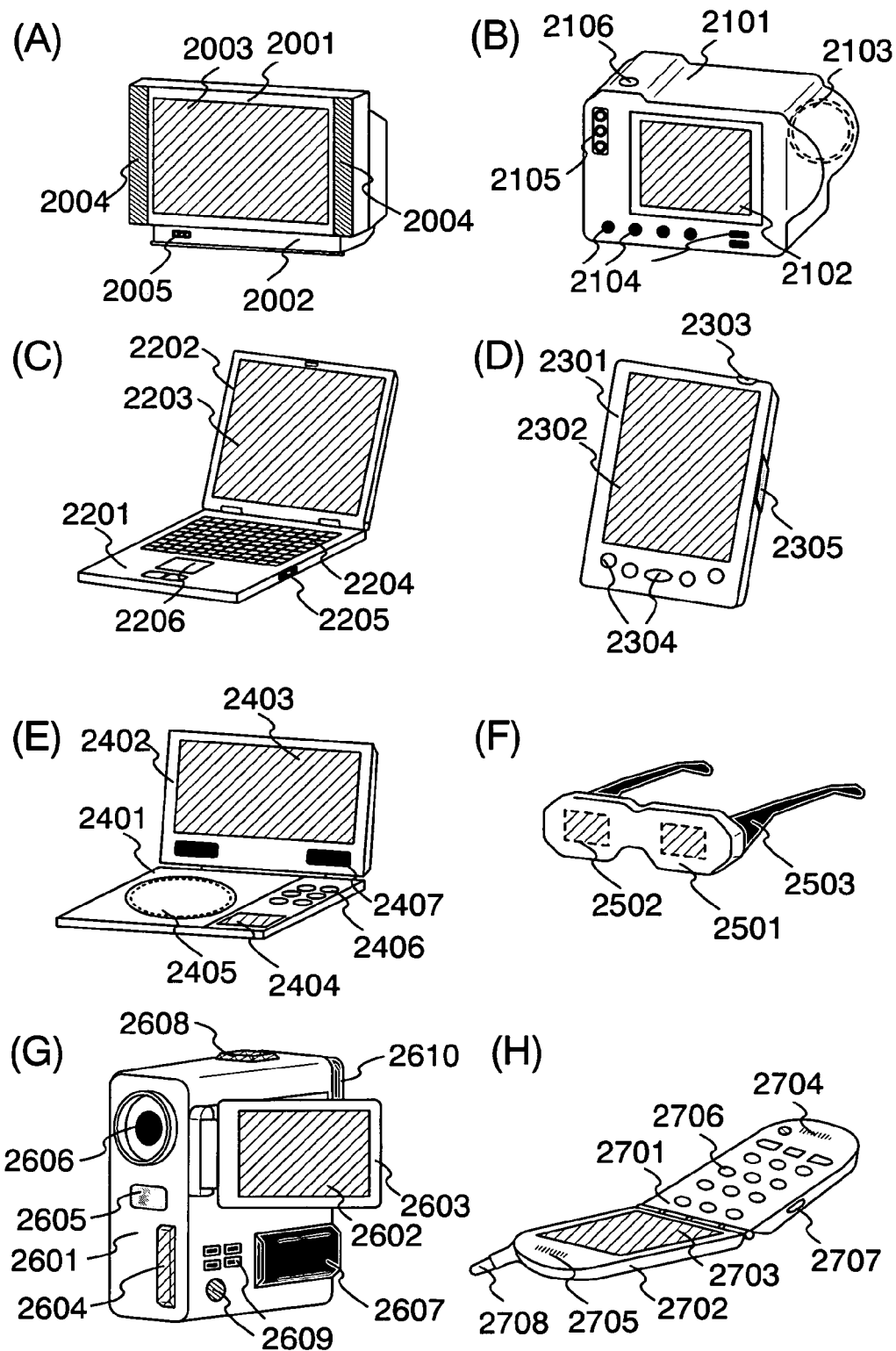
FIG. 5 is a diagram showing an example of an electronic device having the light emitting apparatus to be manufactured by carrying out this invention.

It is possible to manufacture an electronic device by incorporating thereinto the light emitting device obtained by carrying out this invention. Examples of the electronic device are a video camera, a digital camera, a goggle-shaped display (a head mount display), a navigation system, a sound reproduction system (car audio, audio compo, and the like), a notebook type personal computer, a game console, a personal digital assistant (mobile computer, mobile phone, mobile game console, an electronic dictionary, and so forth), an image reproduction system provided with a recording medium (specifically, an apparatus provided with a display capable of reproducing a recording medium such as a digital versatile disc (DVD) and displaying images recorded on the medium), and the like. Specific examples of the electronic devices are shown in FIG. 5.

Shown in FIG. 5(A) is a television which has a housing 2001, a base 2002, a display 2003, a speaker 2004, a video input terminal 2005, and so forth. This invention is applicable to the display 2003. The television inclusively means all kinds of televisions used for information display, such as those for PC, TV broadcasting reception, advertisement display, and the like.

shown in FIG. 5(B) is a digital camera which has a body 2101, a display 2102, an image receiver 2103, an operation key 2104, an external connection port 2105, a shutter 2106, and so forth. This invention is applicable to the display 2102.

Shown in FIG. 5(C) is a notebook type personal computer which has a body 2201, a housing 2202, a display 2203, a keyboard 2204, an external connection port 2205, a pointing mouse 2206, and so forth. This invention is applicable to the display 2203.

Shown in FIG. (D) is a mobile computer which has a body 2301, a display 2302, a switch 2303, an operation key 2304, an infrared ray port 2305, and so forth. This invention is applicable to the display 2302.

Shown in FIG. 5(E) is a mobile image reproduction system (specifically, a DVD reproduction system) provided with a recording medium, which includes a body 2401, a housing 2402, a display A 2403, a display B 2404, a recording medium (ex. DVD) reader 2405, an operation key 2406, a speaker 2407, and so forth. The display A 2403 mainly displays image information, and the display B 2404 mainly displays textual information. This invention is applicable to the display A 2403 and the display B 2404. A home game console and the like are included among the image reproduction systems provided with the recording medium.

Shown in FIG. 5(F) is a goggle-shaped display (a head mount display) which has a body 2501, a display 2502, and an arm 2503. This invention is applicable to the dislay 2502.

Shown in FIG. 5(G) is a video camera which has a body 2601, a display 2602, a housing 2603, an external connection port 2604, a remote control receiver 2605, an image receiver 2606, a battery 2607, an audio input 2608, an operation key 2609, an eyepiece 2601, and so forth. This invention is applicable to the display 2602.

Shown in FIG. 5(H) is a mobile phone which has a body 2701, a housing 2702, a display 2703, an audio input 2704, an audio output 2705, an operation key 2706, an external connection port 2707, an antenna 2708, and so forth. This invention is applicable to the display 2703. In addition, it is possible to suppress power consumption of the mobile phone by displaying texts on the display 2703 in such a fashion that white colored texts are displayed on a black background.

As described above, the light emitting apparatus obtained by carrying out this invention is usable as the display of various electronic devices.

(EMBODIMENTS)

[Embodiment 1]

In this embodiment, an electroluminescent device was manufactured by using 1,4-di-(3,4-ethylenedioxy-2-thienyl) benzene which is a luminescent material represented by the following formula [Chem. 9] as a representative of the compounds represented by the general formulas [Chem. 5] to [Chem. 8]. A structure of the manufactured device is as follows. Cupper phthalocyanine (hereinafter abbreviated to CuPc) is deposited on an ITO substrate as a hole injection layer, and then NPB which is a hole transporting material was deposited. Further, the compound represented by [Chem. 9] was stacked as a luminescent layer. After that, BCP which is an electron transporting material, CaF which is an electron injection material, and an aluminum cathode were formed. Each of the films was formed by vapor deposition. Film thicknesses of the hole injection layer, the hole transporting layer, the luminescent layer, the electron transporting layer, and the electron injection layer were respectively 20 nm, 30 nm, 20 nm, 30 nm, and 2 nm.

[Chem. 9]

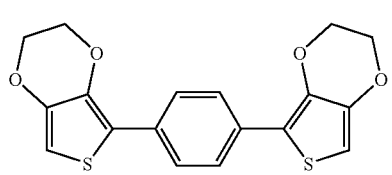

Figure 6:
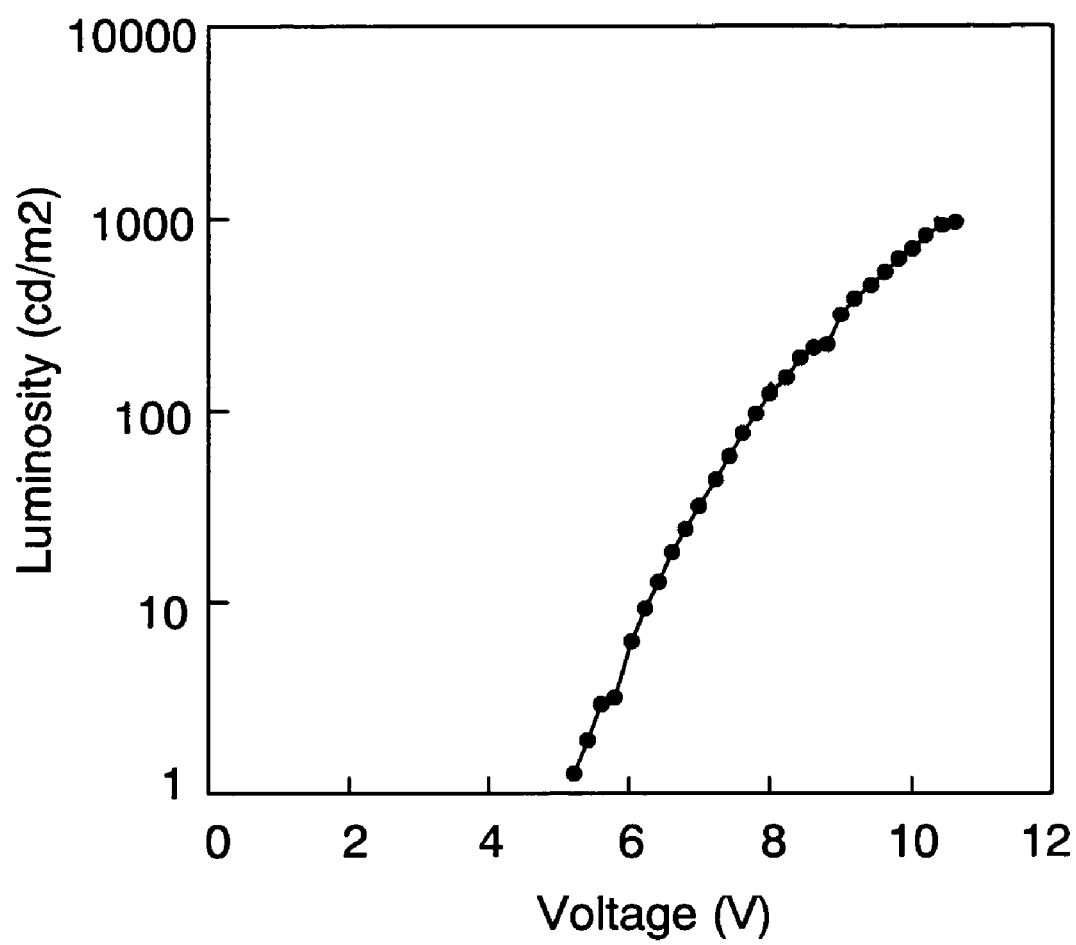
FIG. 6 is a diagram showing a voltage-luminance curve of the light emitting apparatus to be manufactured by carrying out this invention.

A voltage-luminosity curve of the manufactured device is shown in FIG. 6. Light emission starts from near 5 V to attain the maximum luminosity of about 1,000 cd/m$^2$. The color coordinates of the maximum luminosity are x=0.15 and y=0.14, which confirm blue light emission of high purity.

[Embodiment 2]

In this embodiment, an electroluminescent device was manufactured by using, as a hole injection material, 1,4-di-(3,4-ethylenedioxy-2-thienyl)benzene which is the above-described compound [Chem. 9] representative of the compounds represented by the general formulas [Chem. 5] to [Chem. 8]. A structure of the manufactured device is as follows. [Chem. 9] was deposited on an ITO substrate, and then NPB which was a hole transporting material was deposited. Then, Alq$_3$ was deposited as a luminescent material and electron transporting material, followed by forming CaF and an aluminum cathode. Each of the films was formed by vapor deposition. Film thicknesses of the hole injection layer, the hole transporting layer, the luminescent layer (also serving as the electron transporting layer), and the electron injection layer were 20 nm, 30 nm, 50 nm, and 2.5 nm.

Figure 7:
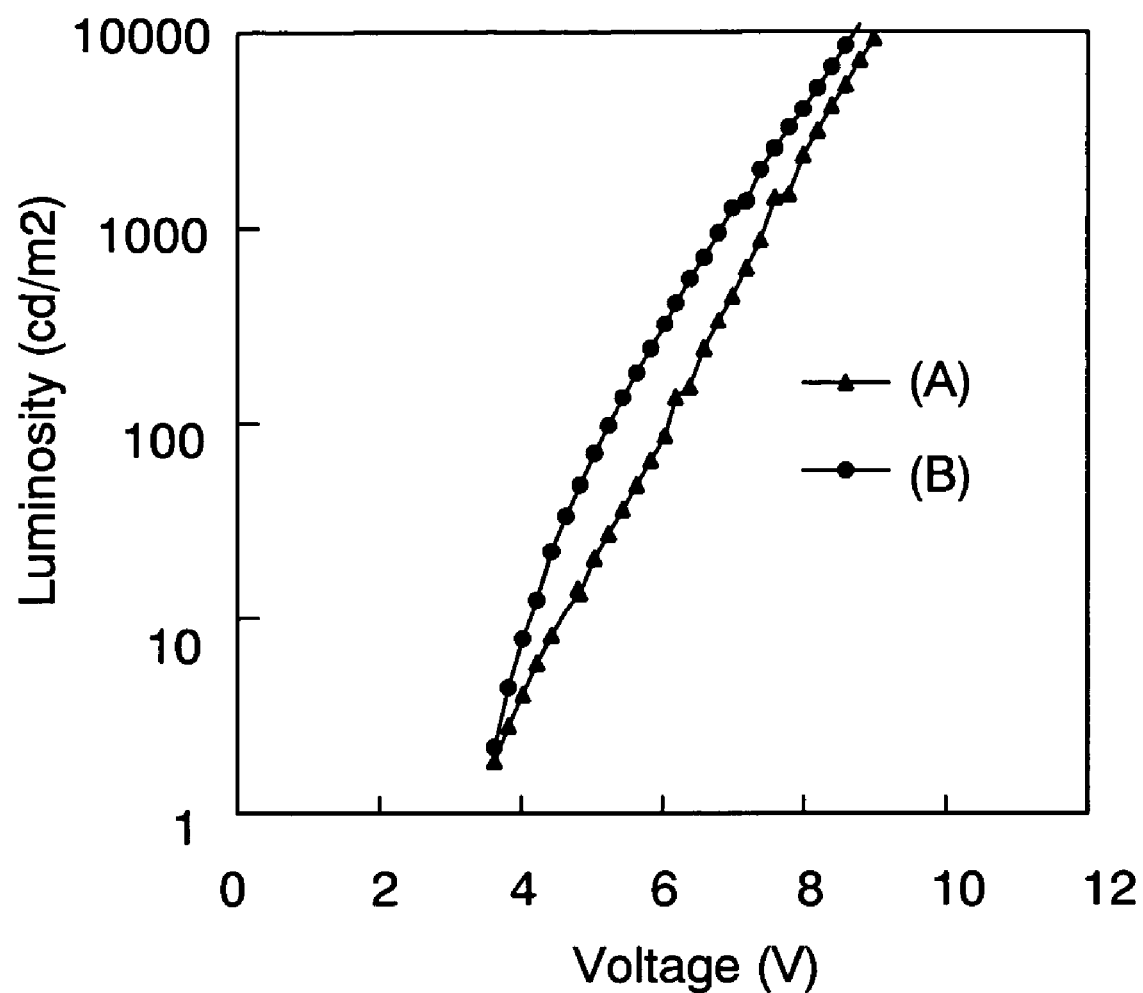
FIG. 7 is a diagram showing a voltage-luminance curve of the light emitting apparatus to be manufactured by carrying out this invention.

A voltage-luminosity curve of the manufactured device is shown in FIG. 7(A). Light emission starts from 3.5 V to attain about 10,000 cd/m$^2$ at 9V. A voltage-luminosity curve obtained by using CuPc as the hole injection material in place of the compound represented by the formula [Chem. 9] is shown in FIG. 7(B). The exhibited characteristics are almost the same as those exhibited by using [Chem. 9]. That is to say, the hole injection characteristic of the compound represented by the formula [Chem. 9] competes with that of CuPc. It is considered that this results from the small ionization potential of the compound represented by the formula [Chem. 9].

[Embodiment 3]

In this embodiment, an electroluminescent device was manufactured by using, as a hole injection material, 4,4'-di-(3,4-ethylenedioxy-2-thienyl)biphenyl which is a compound represented by the following formula [Chem. 10] and representative of the compounds represented by the general formula [Chem. 5] to [Chem. 8]. A structure of the manufactured device is as follows. The compound represented by the formula [Chem. 10] was deposited on an ITO substrate, and then NPB which is a hole transporting material was deposited. Then, Alq$_3$ was deposited as a luminescent material and electron transporting material, followed by forming CaF and an aluminum cathode. Each of the films was formed by vapor deposition. Film thicknesses of the hole injection layer, the hole transporting layer, the luminescent layer (also serving as the electron transporting layer), and the electron injection layer were 20 nm, 30 nm, 50 nm, and 2 nm.

[Chem. 10]

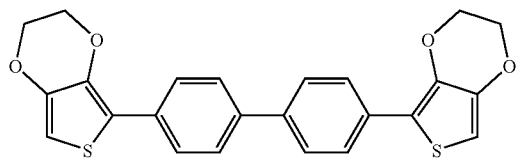

Figure 8:
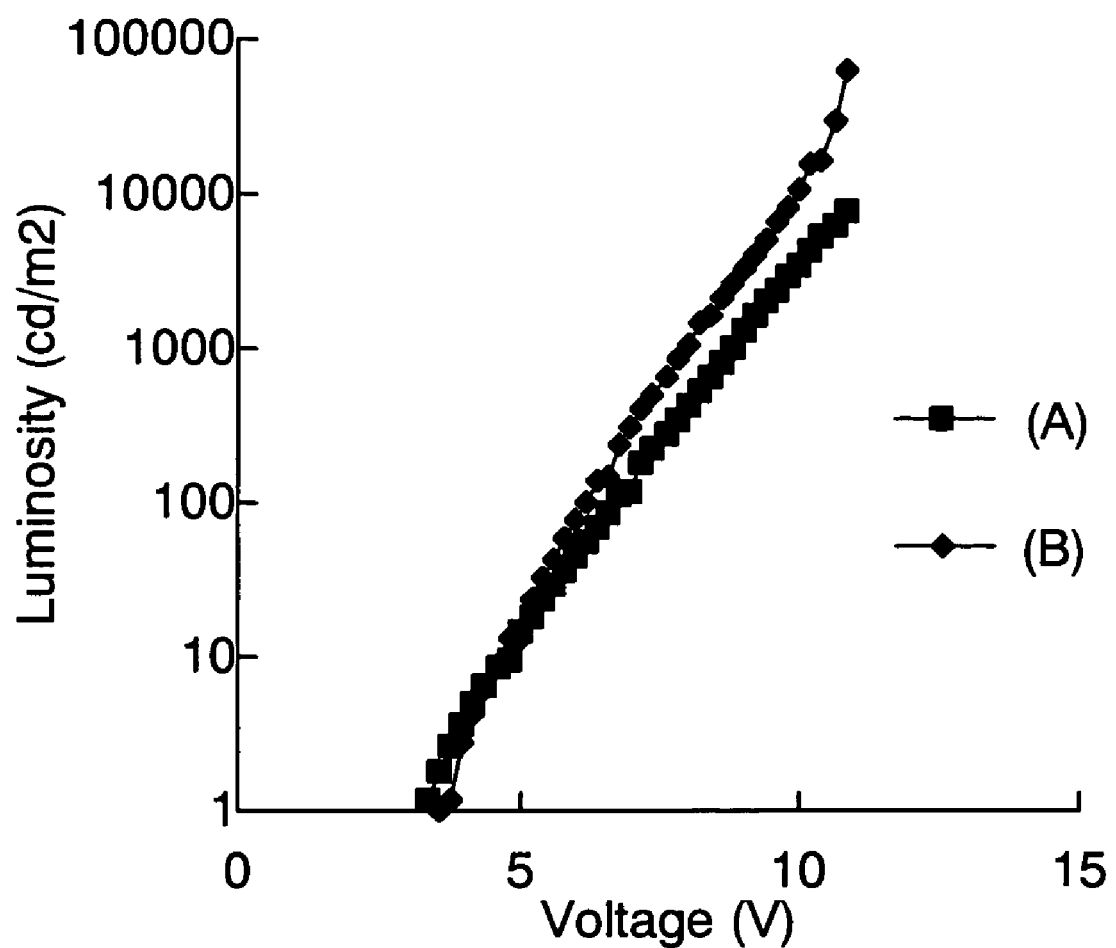
FIG. 8 is a diagram showing a voltage-luminance curve of the light emitting apparatus to be manufactured by carrying out this invention.

Among initial characteristics of the device, a voltage-luminosity curve is shown in FIG. 8(A). Light emission starts from near 3 V to attain about 10,000 cd/m$^2$ at 9V. A voltage-luminosity curve obtained by using CuPc as the hole injection material in place of the compound represented by the formula [Chem. 10] is shown in FIG. 8(B). The exhibited characteristics are almost the same as those exhibited by using [Chem. 10]. That is to say, the hole injection characteristic of the compound represented by the formula [Chem. 10] competes with that of CuPc.

[Embodiment 4]

As described in Embodiments 1 to 3, each of the compounds [Chem. 9] and [Chem. 10] exhibits the excellent characteristics as the material for the electroluminescent device, particularly, as the hole injection material. As is revealed by the results, in the compounds proposed by this invention, i.e. in the compounds represented by the general formulas [Chem. 5] to [Chem. 8], it is preferable that a cyclic structure is formed by $R^1$ and $R^2$ as well as by $R^3$ and $R^4$. This is because an effective conjugate length of the whole molecules is increased by the formation of cyclic structure. This will be clarified by the following Embodiment.

Figure 9:
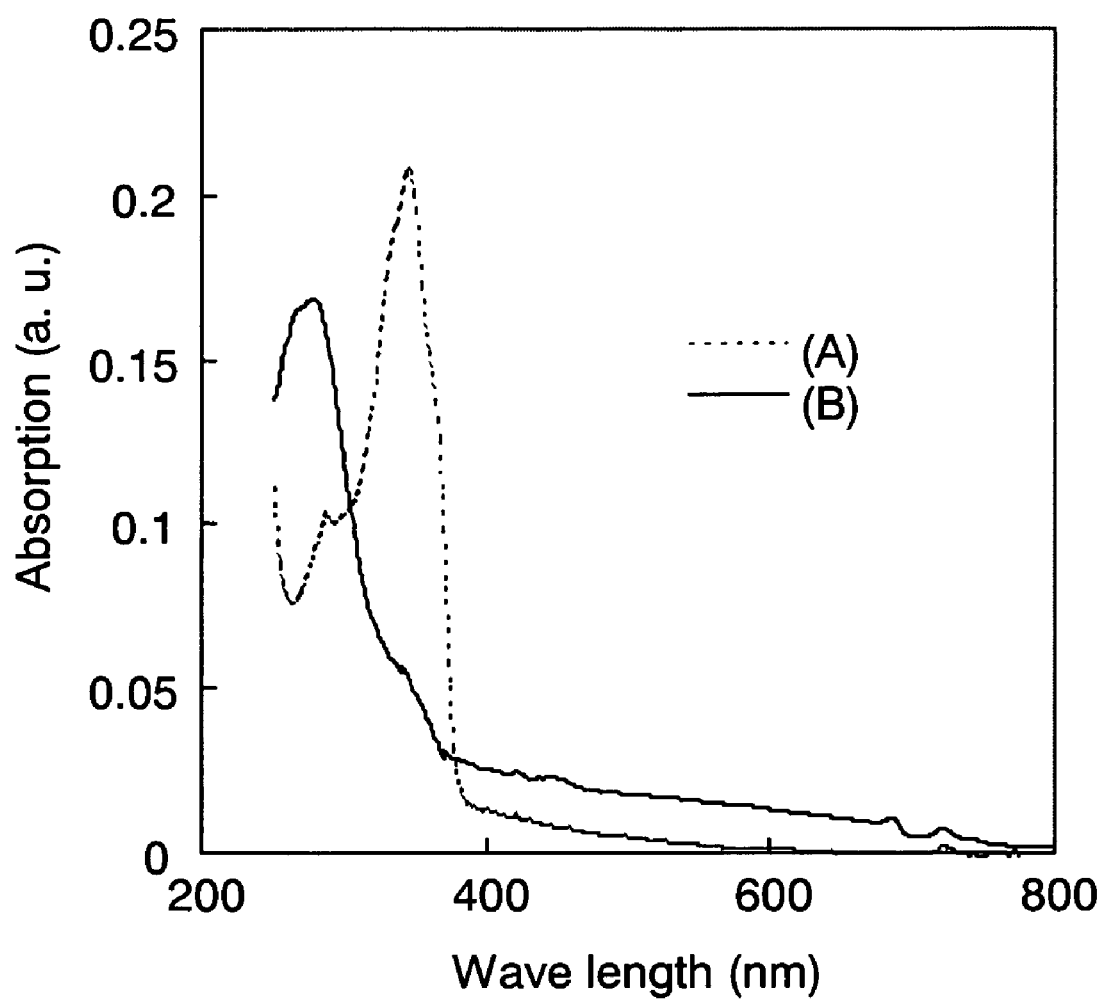
FIG. 9 is a diagram showing an ultraviolet-visible spectrum of an organic material to be used when carrying out this invention.

Shown in FIG. 9 are ultraviolet-visible absorption spectrums of 1,4-di(3,4-ethylenedioxy-2-thienyl)benzene ([Chem.9]) and its analogue, 1,4-bis(3,4-dihexyloxy-2-thienyl)benzene. A structure of 1,4-bis(3,4-dihexyloxy-2-thienyl)benzene is shown in [Chem. 11]. An absorption maximum of the first compound is found at 380 nm as shown in FIG. 9(A), while an absorption maximum of the latter compound is found at 300 nm as shown in FIG. 9(B), thereby revealing that [Chem. 9] which has the cyclic structure has a more expanded conjugate system. As shown in FIG. 9(A), absorption intensity in the visible ray region of [Chem. 9] is remarkably low, and this is prominently different from the conventional hole injection materials.

[Chem. 11]

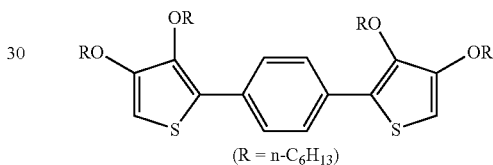

(R = n-C$_6$H$_{13}$)

Further, from measurements of cyclic voltammetry, it is revealed that [Chem. 9] has the more expanded conjugate system. The cyclic voltammetry measurements were conducted by using acetonitrile as a solvent and tetrabutyl ammonium perchlorate as a supporting electrolyte. Each of a working electrode and a counter electrode was made from platinum. Silver/silver chloride was used for a reference electrode. An oxidation potential of [Chem. 9] is 1.20 V (vs. Ag/Ag$^+$), while an oxidation potential of [Chem. 11] is 1.68 V, thereby revealing that the latter is less subject to oxidation. Therefore, in the compounds represented by the general formulas [Chem. 5] to [Chem. 8], it is preferable that the cyclic structures are formed by $R^1$ and $R^2$ and by $R^3$ and $R^4$, and this is supported by the result of this example.

[Embodiment 5]

Figure 10:
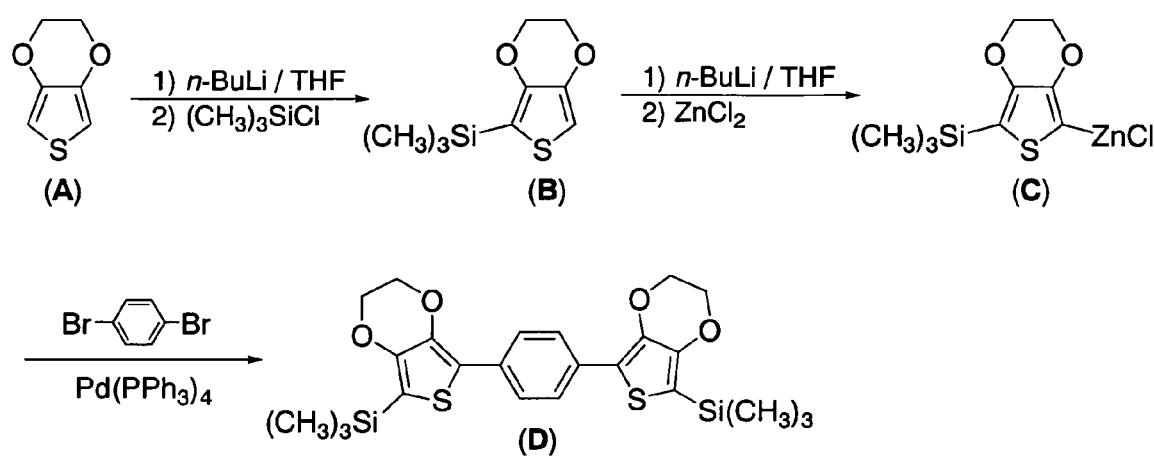
FIG. 10 is a diagram showing a synthetic scheme of a representative example of novel compounds proposed by this invention.

In this embodiment, synthesis of 1,4-di(3,4-ethylenedioxy-5-trimethylsilyl-2-thiely)benzene represented by the following formula [Chem. 12] as a representative of the compounds represented by the general formulas [Chem. 5] to [Chem. 8] will be described. The synthesis scheme is shown in FIG. 10. A hexane solution (48 mL, 74.9 mmol) of 1.56N n-butyllithium was dropped into a dry THF solution (100 mL) of 3,4-ethylenedioxythiophene (Compound A in FIG. 10; 10.30 g, 72.5 mmol) at −78° C. After completion of the dropping, the mixture was stirred for 1 hour at −78° C. Chlorotrimethylsilane (8.93 g, 82.3 mmol) was dropped into the solution and a temperature of the reaction solution was gradually raised to a room temperature. After stirring for 3 hours, the reaction mixture was concentrated under a reduced pressure, followed by extraction with hexane. A hexane layer was dried with magnesium sulfate, followed by filtration. The filtrate was concentrated, and then a residue was distilled under a reduced pressure (200 Pa, 94 to 100° C.), thereby giving the compound represented by (B) in FIG. 10, 2-trimethylsilyl-3,4-ethylenedioxythiophene. Yield: 84%. $^1$H NMR (300 MHz, CDCl$_3$) δ 0.286 (s, 9H), 4.16 (s, 2H), 4.17 (s, 2H), 6.54 (s, 1H): $^{13}$C NMR (75 MHz, CDCl$_3$) δ –0.74, 64.42, 64.51, 104.68, 111.28, 142.63, 147.25.

A hexane solution (55 mL, 86.0 mmol) of 1.56N n-butyllithium was dropped into o a dry THF solution (150 mL) of the compound indicated by (B) in FIG. 10, 2-trimethylsilyl-3,4-ethylenedioxythiophene, (18.6 g, 86.0 mmol) at –78° C. After completion of the dropping, the mixture was stirred for 1 hour at –78° C. and for 30 minutes at 0° C. This solution was dropped into a dry THF suspension (100 mL) of zinc chloride (11.69 g, 85.8 mmol) at a room temperature. After stirring for 1 hour, a compound indicated by (C) in FIG. 10 was obtained in the system. After that, 1,4-diburomobenzene (6.759 g, 28.7 mmol) and tetrakis(triphenylphosphine)palladium (0) (1.28 g, 1.11 mmol) were added, followed by heating reflux of 10 hours. The reaction mixture was thrown into water of about 1 L, and then precipitates were filtrated. The filtrate was dried and then purified by silica gel column chromatography (developer: hexane/ethylacetate 10/1 to 2/1), followed by recrystallization with hexane/ethylacetate (5/1), thereby giving the compound indicated by (D) in FIG. 10, i.e. the compound represented by the following formula [Chem. 12], 1,4-di(3, 4-ethylenedioxy-5-trimethylsilyl-2-thienyl)benzene. Yield: 43%. $^1$H NMR (300 MHz, CDCl$_3$) δ 0.311 (s, 18H), 4.27 (s, 4H), 4.29 (s, 4H), 7.69 (s, 4H).

[Chem. 12]

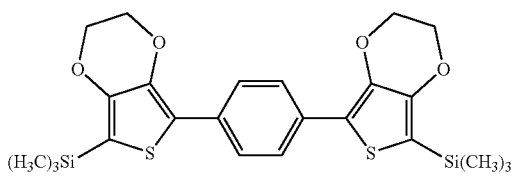

Figure 11:
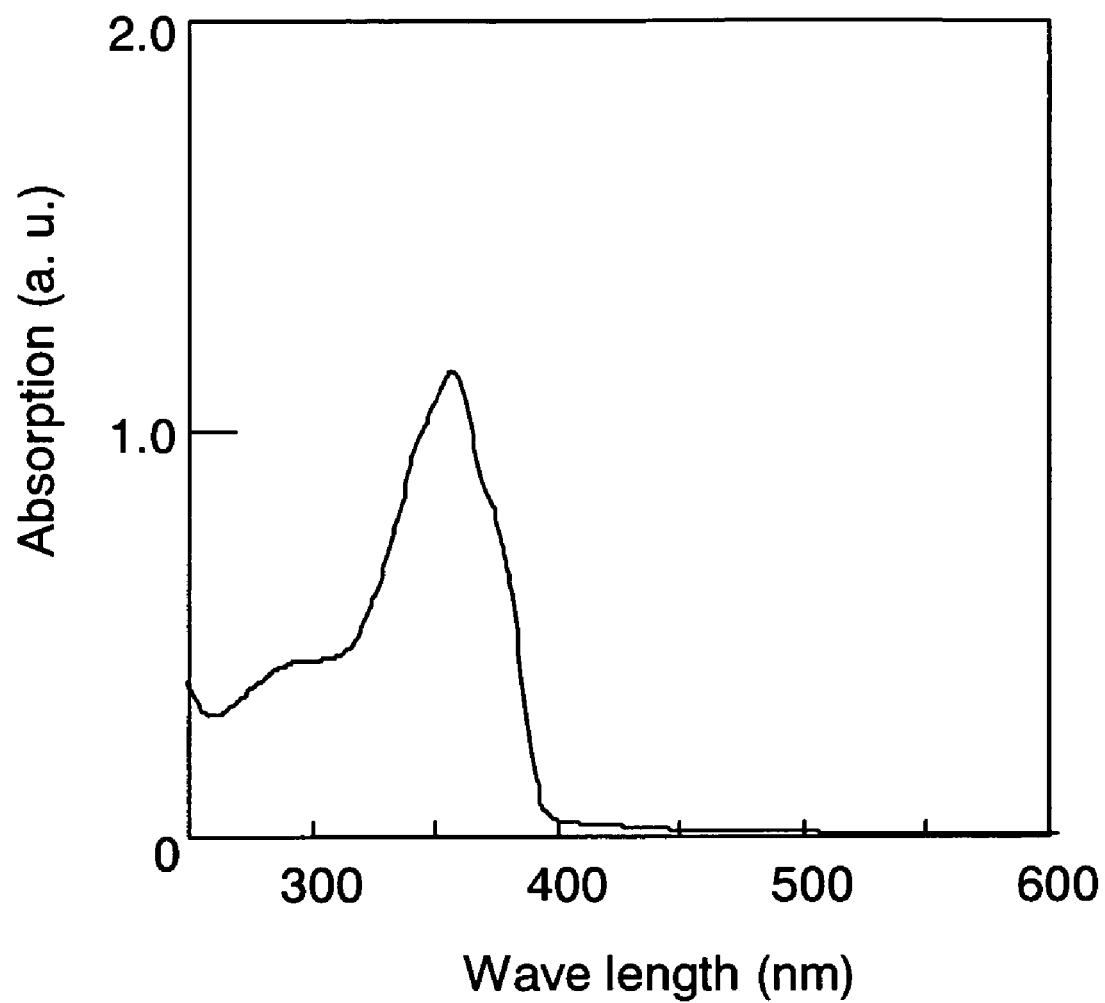
FIG. 11 is a diagram showing an ultraviolet-visible spectrum (in methylene chloride; $2.55 \times 10^{-5}$ M) of the novel compound proposed by this invention.

An ultraviolet-visible absorption spectrum of the thus-synthesized compound represented by the above formula [Chem. 12] is shown in FIG. 11. As shown in FIG. 11, the absorption in the visible region is remarkably small, and, thanks to the small absorption, it is possible to largely reduce the coloring of the device.

[Embodiment 6]

In this embodiment, an effect of introducing a substituent other than hydrogen into $R^5$ and $R^6$ of the compounds represented by the general formulas [Chem. 5] to [Chem. 8] will be described. Solubility is remarkably reduced when $R^5$ and $R^6$ are hydrogen atoms. For instance, solubility to chloroform of the compound represented by the formula [Chem. 9] described in Embodiment 1 is less than 1 wt. %. In contrast, in the case where $R^5$ and $R^6$ are trimethylsilyl groups, the solubility to chloroform at 25° C. is 15.4 wt. %. Thus, it is possible to considerably improve the solubility by introducing the substituent into $R^5$ and $R^6$.

Further, the compound represented by the formula [Chem. 9] is high in crystallinity as suggested by its low solubility, so that it is impossible to obtain a deposition film of good film quality using the compound. Accordingly, in the case of using the compound represented by [Chem. 9] as a luminescent layer, it is difficult to achieve a uniform surface emission. In contrast, the compound represented by the formula [Chem. 12] gives a deposition film having a good quality thanks to the high solubility.

[Embodiment 7]

In this Embodiment, manufacturing of a device wherein a hole injection layer is formed by using 1,4-di(3,4-ethylenedioxy-5-trimethylsilyl-2-thienyl)benzene represented by the formula [Chem. 12] and initial characteristics of the device will be described. A structure of the manufactured device is as follows. The compound represented by the formula [Chem. 12] is deposited on an ITO substrate, and then NPB which is a hole transporting material is deposited. Further, Alq$_3$ is deposited as a luminescent material and electron transporting material, followed by formation of CaF and an aluminum cathode. Each of the films was formed by vapor deposition. Thicknesses of the hole injection layer, the hole transporting layer, the luminescent layer (serving also as an electron transporting layer), and the electron injection layer were 20 nm, 30 nm, 50 nm, and 2 nm. As a comparative experiment, a device using copper phthalocyanine (hereinafter abbreviated to CuPc) in place of the compound represented by the formula [Chem. 12] was manufactured.

The thus-manufactured device starts light emission from 3.6 V, and a potential thereof was identical with a light emission start voltage (3.6 V) of the device formed by using CuPc. This means that hole injection characteristic of the novel compound represented by the formula [Chem. 12] is almost identical with that of CuPc.

[Embodiment 8]

In this embodiment, a synthesis of 4,4'-bis(5-phenyl-3,4-ethylenedioxy-2-thienyl)biphenyl (hereinafter referred to as DPEBP) which is a compound represented by the following formula [Chem. 13] as a representative of the compounds represented by the general formulas [Chem. 5] to [Chem. 8] will be described.

[Chem. 13]

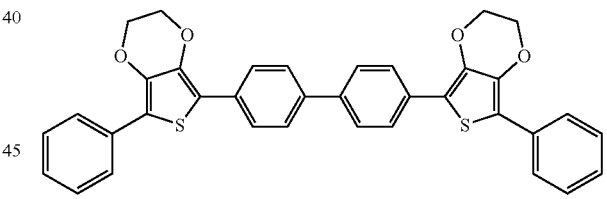

To start with, a synthesis of an intermediate represented by the following formula [Chem. 14] (hereinafter referred to as an intermediate a) will be described. 250 ml of a dry THF was added to 22.41 g of 2,3-dihydrothieno-[3,4-b]-1,4-dioxin, and then the mixture was cooled to –78° C. 100 ml of n-butyllithium (1.58 M hexane solution) was dropped, followed by stirring for 1 hour. The thus-obtained mixture was added to 25.84 g of zinc chloride at a room temperature, followed by stirring for 1 hour. 18.3 ml of bromobenzene and 1.83 g of tetrakis(triphenylphosphine)palladium were added to the mixture, followed by stirring under heating reflux for 5 hours. Ethylacetate, 1M hydrochloric acid, and water were added to the solution which had been cooled to a room temperature, and then an organic layer was batched off. After drying with magnesium sulfate, the solvent was concentrated and then purified by column chromatography (hexane/ethylacetate). The NMR data are indicated below. $^1$H NMR (CDCl$_3$, δ) 7.72 ppm (d, 2H), 7.36 ppm (t, 2H), 7.21 ppm (t, 1H), 6.29 ppm (s, 1H), 4.29 ppm (m, 4H).

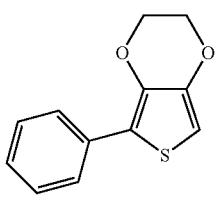

Next, 100 ml of THF was added to 10.36 g of the intermediate a obtained above, followed by cooling the mixture to −78° C. 33.1 ml of n-butyllithium (1.58 M hexane solution) was dropped into the mixture, followed by stirring for 1 hour. 8.77 g of 4,4'-diiodebiphenyl and 549 mg of tetrakis(triphenylphosphine)palladium were added to this mixture, followed by stirring the mixture for 5 hours under heating reflux. A solid obtained by filtering the mixture was washed with ethanol. The solid was subjected to a recrystallization with chloroform to obtain an organic compound DPEBP of this invention (yellow powder). The NMR data are shown below. $^1$H NMR (CDCl$_3$, δ) 7.77 ppm (m, 12H), 7.44 ppm (t, 4H), 7.28 ppm (t, 2H), 4.45 ppm (s, 8H).

[Embodiment 9]

In this embodiment, a synthesis of 1,4-bis(5-phenyl-3,4-ethylenedioxy-2-thienyl)benzene (hereinafter referred to as DPEBZ) represented by the following formula [Chem. 15], which is representative of the compounds represented by the general formulas [Chem. 5] to [Chem. 8], will be described.

[Chem. 15]

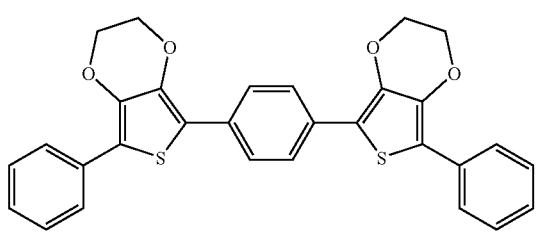

100 ml of THF was added to 6.07 g of the intermediate a obtained by Embodiment 8, followed by cooling the mixture to −78° C. 19.4 ml of n-butyllithium (1.58 M hexane solution) was dropped into the mixture, followed by stirring for 1 hour. The thus-obtained mixture was added to 4.50 g of zinc chloride at a room temperature, followed by stirring for one hour at the room temperature. 4.12 g of 1,4'-diiodebenzene and 321 mg of tetrakis(triphenylphosphine)palladium were added to this mixture, followed by stirring the mixture for 5 hours under heating reflux. A solid obtained by filtering the mixture was washed with ethanol. The solid was subjected to a recrystallization with chloroform to obtain an organic compound DPEBZ of this invention (orange powder). The NMR data are shown below. $^1$H NMR (CDCl$_3$, δ) 7.77 ppm (m, 8H), 7.38 ppm (t, 4H), 7.23 ppm (t, 2H), 4.38 ppm (s, 8H).

[Embodiment 10]

In this embodiment,)biphenyl (hereinafter referred to as DtBuPEBP) represented by the followin a synthesis of 4,4'-bis[5-(4-tert-butylphenyl)-3,4-ethylenedioxy-2-thienyl g formula [Chem. 16], as a representative of the compounds represented by the general formulas [Chem. 5] to [Chem. 8], will be described.

[Chem. 16]

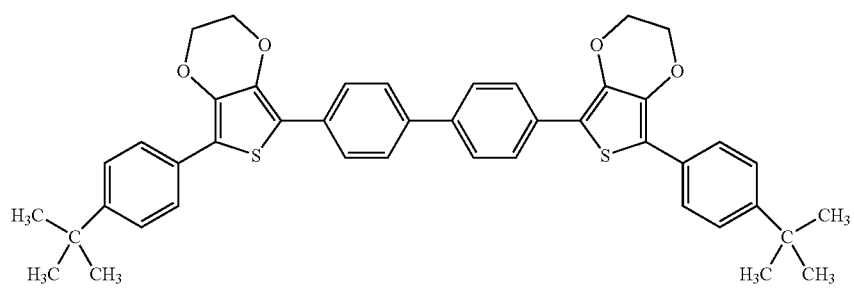

To start with, a synthesis of an intermediate (hereinafter referred to as an intermediate b) represented by the following formula [Chem. 17] will be described. 100 ml of THF was added to 10.57 g of 2,3-dihydrothieno-[3,4-b]-1,4-dioxin, and then the mixture was cooled to −78° C. 37.2 ml of LDA (2.0 M) was dropped, followed by stirring for 1 hour. 12.14 g of zinc chloride was added, followed by stirring for one hour at a room temperature. 14.3 ml of 1-bromo-4-tert-butylbenzene and 859 g of tetrakis(triphenylphosphine)palladium were added, followed by stirring the mixture for 8 hours under heating reflux. Ethylacetate and water were added to the solution which has been cooled to a room temperature, and then an organic layer was batched off. After drying with magnesium sulfate, the solvent was concentrated. After that, purification by column chromatography (toluene) was performed. The NMR data are shown below. $^1$H NMR (CDCl$_3$, δ) 7.67 ppm (d, 2H), 7.45 ppm (d, 2H), 6.32 ppm (s, 1H), 1.40 ppm (s, 9H).

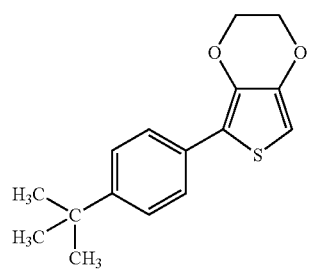

Next, 50 ml of THF was added to 2.56 g of the intermediate b obtained above, followed by cooling the mixture to −78° C. 5.12 ml of LDA (2.0 M) was dropped, followed by stirring for 1 hour. 1.53 g of zinc chloride was added, followed by stirring for one hour at a room temperature. 1.71 g of 4,4'-diiodebiphenyl and 107 mg of tetrakis(triphenylphosphine)palladium were added, followed by stirring for 6 hours under heating reflux. Ethylacetate, 1M hydrochloric acid, and water were added to the solution which has been cooled to a room temperature, and then an organic layer was batched off. After drying the organic layer with magnesium sulfate, the solvent was concentrated. A recrystallization with chloroform was performed to obtain an organic compound DtBuPEBP of this invention. The NMR data are shown below.

$^1$H NMR (CDCl$_3$, δ) 7.80 ppm (d, 4H), 7.66 ppm (m, 8H), 7.41 ppm (d, 4H), 4.36 ppm (s, 8H), 1.32 ppm (s, 9H).

[Embodiment 11]

In this embodiment, an electroluminescent device was formed by using DPEBP which is the above-described compound [Chem. 13] and a representative of the compounds represented by the general formulas [Chem. 5] to [Chem. 8] as a luminescent material. A constitution of the manufactured device is as follows. Cupper phthalocyanine which is a hole injection material and NPB which is a hole transporting material were deposited in this order by vapor deposition on an ITO layer which had been formed on a glass substrate. Thicknesses of the films were 20 nm and 40 nm. On this laminated film, 2-t-butyl-9,10-di(2-naphthyl)anthracene and DPEBP each having a thickness of 40 nm were simultaneously deposited to form a luminescent layer. Further, an electron transporting material Alq was laminated, of which a thickness was 20 nm. Then, an electron injection material CaF$_2$ was deposited, followed by depositing an Al electrode. A ratio of 2-t-butyl-9,10-di(2-naphthyl)anthracene to DPEBP was 100 to 1.

Blue light emission of high purity having color coordinates of x=0.15 and y=0.16 was obtained by supplying a current to the device. A light emission start voltage was 4 V, and 10,000 cd/m$^2$ of luminosity was obtained by an application of 10 V. Efficiency was 3.9 cd/A, which is a good value as the blue light emitting device.

The invention claimed is:

1. An electroluminescent device comprising a conjugated molecule represented by the general formula [Chem. 1]

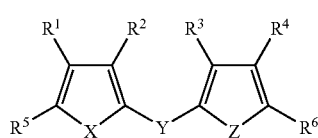

[Chem. 1]

(wherein X and Z may be the same or different and represent a sulfur atom, an oxygen atom, a nitrogen atom and a silicon atom each having an alkyl group or an arylen group; Y represents an arylen group; and R$^1$ to R$^6$ independently represent a hydrogen atom, an aryl group, an alkyl group, a cyano group, a dialkylamino group, a thioalkoxy group, or an alkoxy group).

2. An electroluminescent device comprising a conjugated molecule represented by the general formula [Chem. 2]

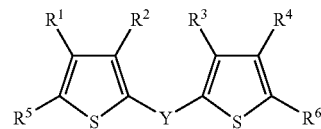

[Chem. 2]

(wherein Y represents an arylen group; and R$^1$ to R$^6$ independently represent a hydrogen atom, an aryl group, an alkyl group, a cyano group, a dialkylamino group, a thioalkoxy group, or an alkoxy group).

3. An electroluminescent device comprising a conjugated molecule represented by the general formula [Chem. 3]

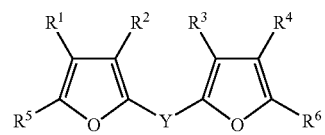

[Chem. 3]

(wherein Y represents an arylen group; and R$^1$ to R$^6$ independently represent a hydrogen atom, an aryl group, an alkyl group, a cyano group, a dialkylamino group, a thioalkoxy group, or an alkoxy group).

4. An electroluminescent device comprising a conjugated molecule represented by the general formula [Chem. 4]

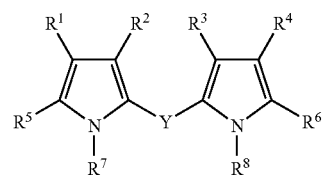

[Chem. 4]

(wherein Y represents an arylen group; R$^1$ to R$^6$ independently represent a hydrogen atom, an aryl group, an alkyl group, a cyano group, a dialkylamino group, a thioalkoxy group, or an alkoxy group; and R$^7$ and R$^8$ represent an alkyl group or an aryl group).

5. The conjugated molecule represented by the general formula [Chem. 1]

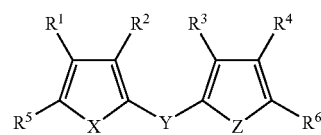

[Chem. 1]

(wherein X and Z may be the same or different and represent an oxygen atom, a sulfur atom, or a silicon atom and a nitrogen atom each having an alkyl group or an arylen group; Y represents an arylen group and represents a bivalent group having a hydrocarbon aromatic ring having 6 to 20 carbon atoms or a bivalent heteroaromatic group having 4 to 30 carbon atoms and including at least one selected from the group consisting of oxygen, nitrogen, sulfur, and silicon; R$^1$ to R$^4$ independently represent a hydrogen atom, an aryl group, an alkyl group, a cyano group, a dialkylamino group, a thioalkoxy group, or an alkoxy group; and $R^5$ and $R^6$ represent an aromatic hydrocarbon group or a heteroaromatic group including at least one selected from the group consisting of oxygen, nitrogen, sulfur, and silicon, an alkyl group, a cyano group, a dialkylamino group, a thioalkoxy group, or a silyl group).

6. The conjugated molecule according to claim 1, wherein a solubility to chloroform at 25° C. and 1 atm. is in the range of 1 wt. % to 20 wt. %.

7. The conjugated molecule according to claim 2, wherein a solubility to chloroform at 25° C. and 1 atm. is in the range of 1 wt. % to 20 wt. %.

8. The conjugated molecule according to claim 3, wherein a solubility to chloroform at 25° C. and 1 atm. is in the range of 1 wt. % to 20 wt. %.

9. The conjugated molecule according to claim 4, wherein a solubility to chloroform at 25° C. and 1 atm. is in the range of 1 wt. % to 20 wt. %.

10. The conjugated molecule according to claim 5, wherein a solubility to chloroform at 25° C. and 1 atm. is in the range of 1 wt. % to 20 wt. %.

11. The conjugated molecule according to claim 1, wherein the conjugated molecule is used for a hole injection layer, a hole transporting layer, or a luminescent layer of an electroluminescent device.

12. The conjugated molecule according to claim 2, wherein the conjugated molecule is used for a hole injection layer, a hole transporting layer, or a luminescent layer of an electroluminescent device.

13. The conjugated molecule according to claim 3, wherein the conjugated molecule is used for a hole injection layer, a hole transporting layer, or a luminescent layer of an electroluminescent device.

14. The conjugated molecule according to claim 4, wherein the conjugated molecule is used for a hole injection layer, a hole transporting layer, or a luminescent layer of an electroluminescent device.

15. The conjugated molecule according to claim 5, wherein the conjugated molecule is used for a hole injection layer, a hole transporting layer, or a luminescent layer of an electroluminescent device.

16. An electronic device using the electroluminescent device of claim 1.

17. An electronic device using the electroluminescent device of claim 2.

18. An electronic device using the electroluminescent device of claim 3.

19. An electronic device using the electroluminescent device of claim 4.

20. An electronic device using the electroluminescent device including the conjugated molecule of claim 5.

* * * * *